United States Patent
Fang et al.

(10) Patent No.: US 11,904,991 B2
(45) Date of Patent: Feb. 20, 2024

(54) SCRUBBER-HEATING APPARATUS FOR DIVING REBREATHER

(71) Applicant: JUNIOR CO., LTD., Chiayi (TW)

(72) Inventors: Ching Han Fang, Chiayi (TW); Hsin Yu Lo, Chiayi (TW); Ching Lin Fang, Chiayi (TW); Shao Hang Hung, Chiayi (TW); Yu Shan Zhou, Chiayi (TW); Pei Jing Lin, Chiayi (TW)

(73) Assignee: JUNIOR CO., LTD., Chiayi (TW)

(*) Notice: Subject to any disclaimer, the term of this patent is extended or adjusted under 35 U.S.C. 154(b) by 0 days.

(21) Appl. No.: 17/971,942

(22) Filed: Oct. 24, 2022

(65) Prior Publication Data

US 2023/0166820 A1 Jun. 1, 2023

(30) Foreign Application Priority Data

Nov. 26, 2021 (TW) .................. 110214070

(51) Int. Cl.
| | | |
|---|---|---|
| *B63C 11/28* | (2006.01) | |
| *B63C 11/22* | (2006.01) | |
| *A62B 9/00* | (2006.01) | |
| *A62B 19/00* | (2006.01) | |
| *B63C 11/24* | (2006.01) | |
| *A61M 16/22* | (2006.01) | |

(52) U.S. Cl.
CPC .............. *B63C 11/28* (2013.01); *A62B 9/003* (2013.01); *A62B 19/00* (2013.01); *B63C 11/22* (2013.01); *B63C 11/24* (2013.01); *A61M 16/22* (2013.01)

(58) Field of Classification Search
CPC ......... B63C 11/02; B63C 11/18; B63C 11/22; B63C 11/24; B63C 2011/2254; A62B 7/00; A62B 7/02; A62B 7/10; A62B 9/003; A62B 9/00; A62B 19/00; A61M 16/22

See application file for complete search history.

(56) References Cited

U.S. PATENT DOCUMENTS 4,350,662 A 9/1982 Dowgul et al.
5,111,809 A * 5/1992 Gamble ................... A62B 9/02
128/205.15

(Continued)

FOREIGN PATENT DOCUMENTS

| CN | 1264345 A | 8/2000 | |
|---|---|---|---|
| GB | 2428011 A * | 1/2007 | ............. B63C 11/24 |

*Primary Examiner* — Colin W Stuart
(74) *Attorney, Agent, or Firm* — MUNCY, GEISSLER, OLDS & LOWE, P.C.

(57) ABSTRACT

A scrubber-heating apparatus for a diving rebreather includes an oxygen supplying element. The oxygen supplying element has a gas mixing portion connected thereto. The gas mixing portion has a breath connecting element connected thereto. The breath connecting element has a scrubber connected thereto. The scrubber is provided with an absorbent heating element and a temperature detecting component. The temperature detecting component has a state display connected thereto. The absorbent heating element and the state display are electrically connected to a power supplying portion. Thereby, the scrubber can recycle gas exhaled by a user to prolong the duration of use of the rebreather. Additionally, the absorbent heating element increases the temperature in the scrubber, thereby enhancing the adsorption efficiency and prolonging the overall duration of use.

8 Claims, 7 Drawing Sheets

(56) References Cited

U.S. PATENT DOCUMENTS

| | | | | |
|---|---|---|---|---|
| 6,003,513 A | * | 12/1999 | Readey | A62B 19/00 128/205.24 |
| 6,712,071 B1 | * | 3/2004 | Parker | B63C 11/24 128/203.14 |
| 6,895,961 B1 | * | 5/2005 | Todorov | A62B 19/00 128/201.27 |
| 2003/0101996 A1 | * | 6/2003 | Franberg | B01D 53/0446 128/205.12 |
| 2003/0188744 A1 | * | 10/2003 | Deas | A62B 7/02 128/201.27 |
| 2016/0023156 A1 | * | 1/2016 | Castellanet | B01D 53/0438 96/111 |

* cited by examiner

SCRUBBER-HEATING APPARATUS FOR DIVING REBREATHER

BACKGROUND OF THE INVENTION

1. Technical Field

The present invention relates to diving rebreathers, and more particularly to a scrubber-heating apparatus for a diving rebreather that has prolonged duration of use.

2. Description of Related Art

Nowadays, diving is not only for military and commercial purposes, but also a popular leisure sport. Regardless of the purpose, diving is conducted in two major ways. The first is free diving for which divers use no underwater breathing apparatuses, and the second is scuba diving where users dive with breathing apparatuses.

While free diving is mostly for leisure, scuba diving was mainly conduced for military and commercial purposes in the past. With the economic growth, more and more people conduct scuba diving at their leisure time just for fun. The term "scuba," as the abbreviation of "self-contained underwater breathing apparatus," represents various types of apparatus, such as open-circuit breathing apparatuses and closed-circuit breathing apparatuses, also referred to as closed-circuit rebreathers herein or diving rebreathers.

An open-circuit breathing apparatus discharges gas exhaled by the diver without recycling. Differently, a closed-circuit rebreather makes recycling by collecting gas exhaled by the diver, treating it by removing carbon dioxide contained therein, supplementing a proper amount of oxygen, and re-supplying it to the diver.

To this end, removal of carbon dioxide is usually achieved by absorption. The absorption efficiency of a rebreather determines its duration of use. In other words, when a rebreather has high efficiency in absorbing carbon dioxide, it has long duration of use. Hence, it is desirable to improve the existing rebreathers in terms of adsorption efficiency.

It is known that the temperature of its use environment is a factor to how efficient a rebreather removes carbon dioxide through adsorption. Taking the absorption efficiency in the normal atmospheric temperature as a benchmark, adsorption for carbon dioxide can become more inefficient at a lower working temperature.

It is particularly apparent in cold waters where the water temperature creates a low-temperature working environment, leading to inefficient carbon-dioxide adsorption and reduced duration of rebreather use.

SUMMARY OF THE INVENTION

The primary objective of the present invention is to use an absorbent heating element to increase the temperature of a scrubber, thereby enhancing its adsorption efficiency and in turn prolonging its duration of use.

To achieve the foregoing objective, the present invention comprises: an oxygen supplying element, a gas mixing portion deposited at one side of the oxygen supplying element and connected to the oxygen supplying element, a scrubber deposited at one side of the gas mixing portion and connected to the gas mixing portion, an absorbent heating element deposited on the scrubber, a temperature detecting component deposited inside the scrubber, a state display connected to the temperature detecting component, and a power supplying portion electrically connected to the absorbent heating element and the state display.

With the configuration described above, a user intending to use the rebreather may hold the breath connecting element in his/her mouth and breath so as to inhale the oxygen supplied by the oxygen supplying element to the gas mixing portion. The waste gas exhaled by the user is guided into the scrubber where carbon dioxide is removed from the waste gas through adsorption. Then the treated gas is guided into the gas mixing portion to mix with oxygen for reuse.

The adsorption efficiency is highly related to the temperature in the scrubber. In particular, the higher the temperature is higher, the higher the adsorption efficiency is. Correspondingly, the high absorption efficiency leads to the long duration of use of the rebreather. The present invention thus uses the absorbent heating element powered by the power supplying portion to heat the scrubber, so as to enhance the adsorption efficiency and remove carbon dioxide form waste gas to the greatest extent through adsorption, and in turn to maximize reuse of the waste gas. The present invention also uses the state display to inform the user of the temperature state in the scrubber, thereby enabling real-time monitoring.

With the technical scheme describe above, the problem about low adsorption efficiency with respect to carbon dioxide as seen in the conventional closed-circuit scubas can be overcome.

DETAILED DESCRIPTION OF THE INVENTION

Figure 1:
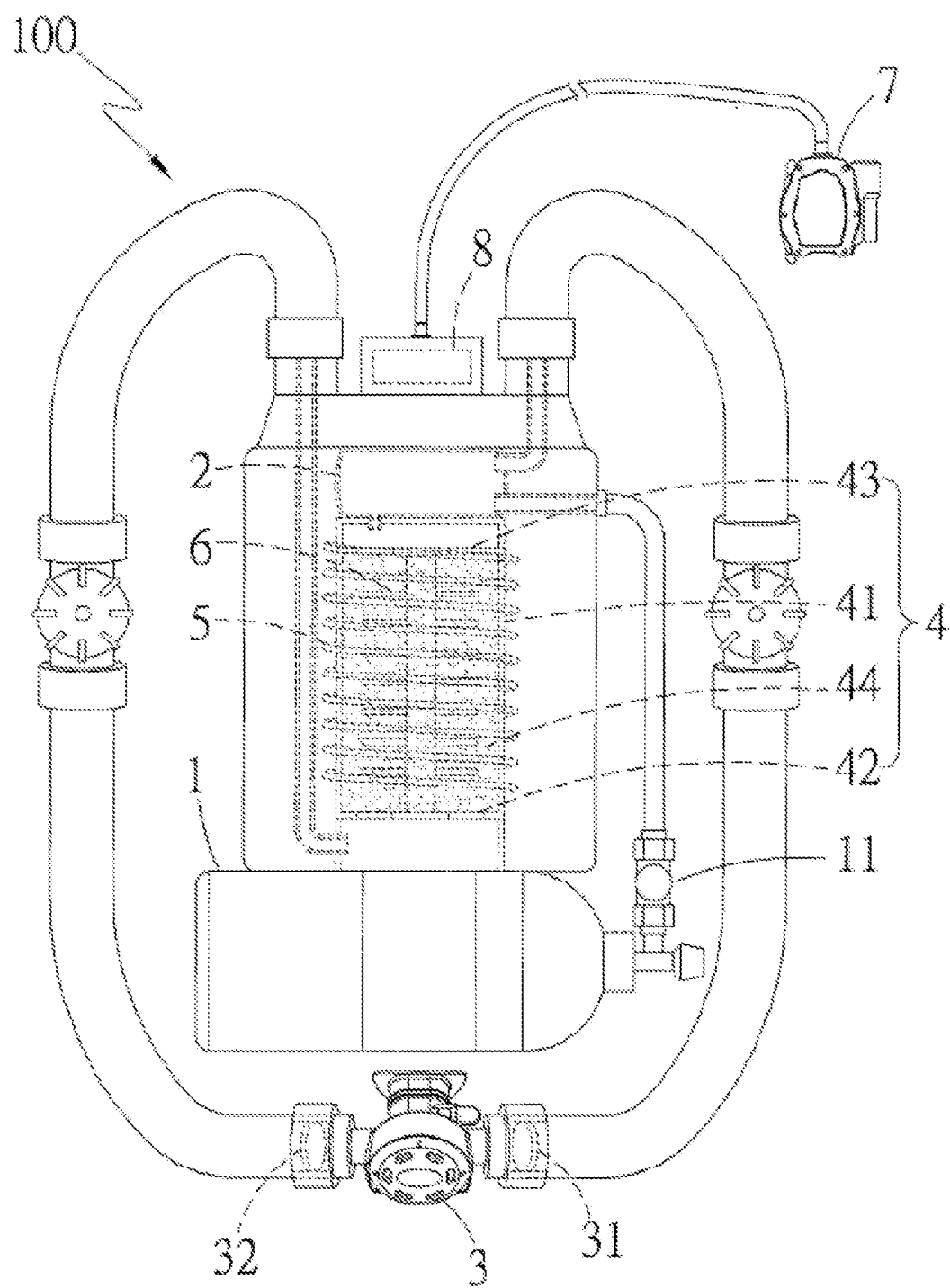
FIG. 1 is a schematic drawing of an apparatus according to a preferred embodiment of the present invention.
Figure 2:
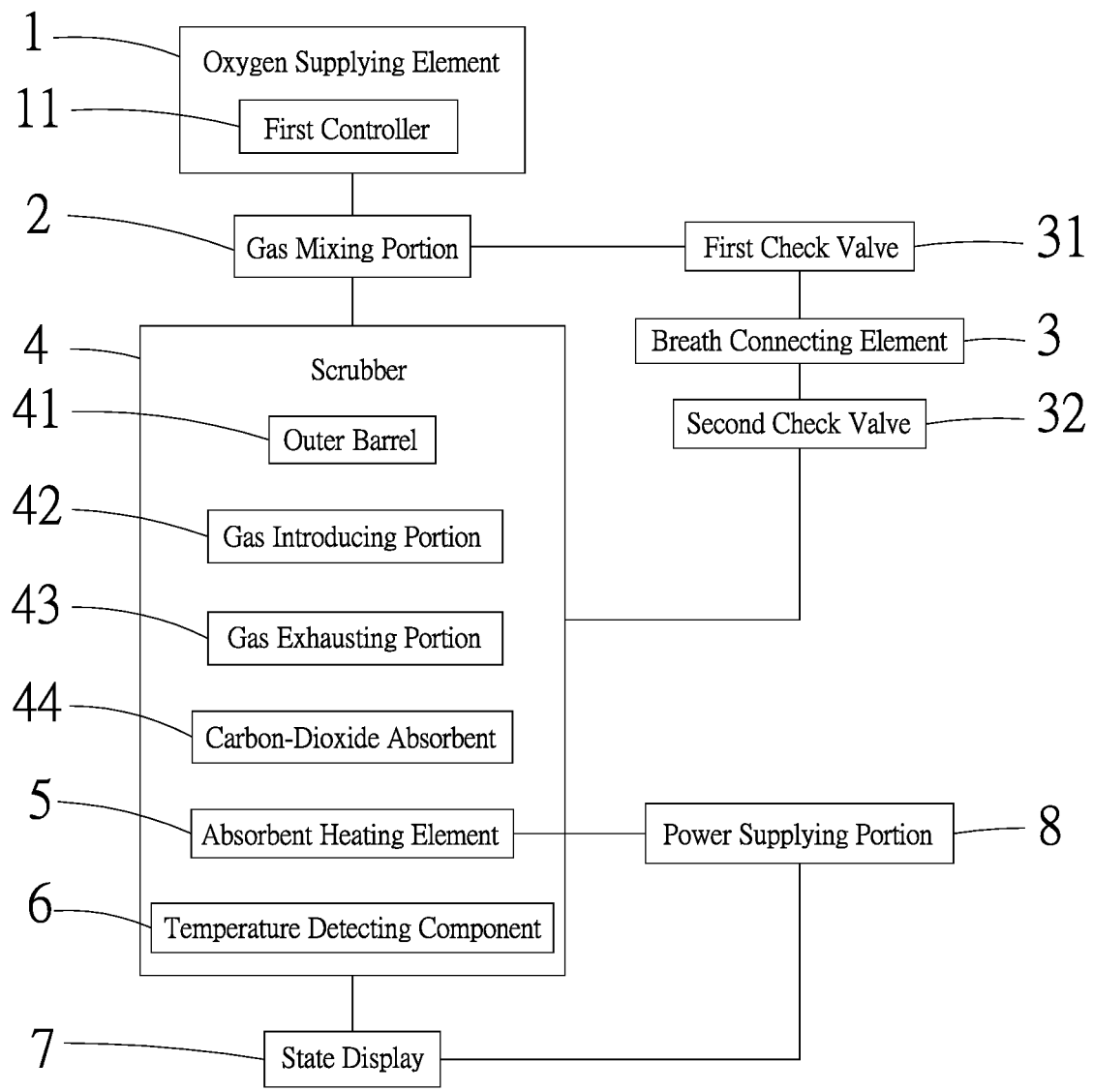
FIG. 2 is a structural diagram of the apparatus according to the preferred embodiment of the present invention.
Figure 3:
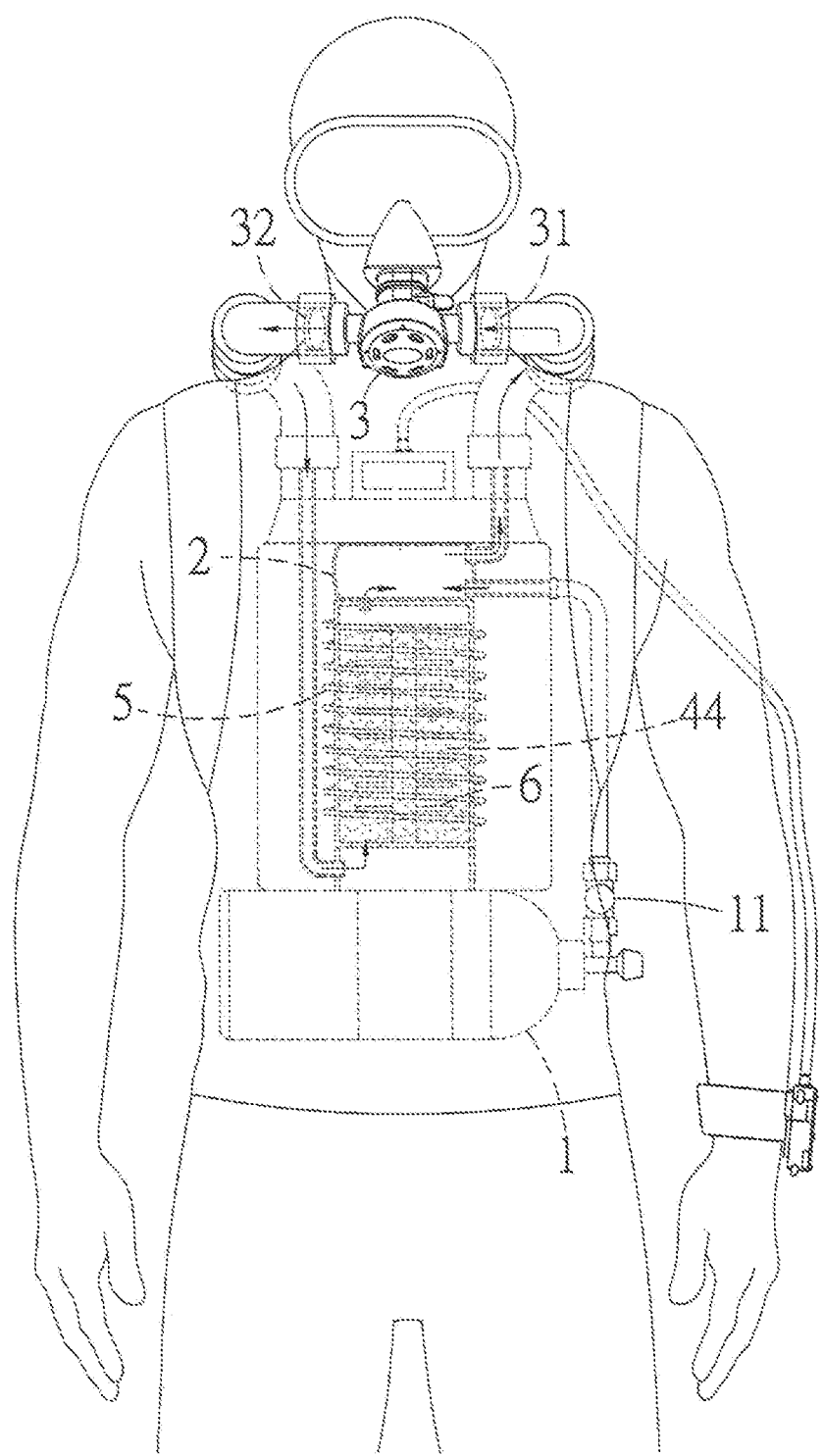
FIG. 3 is an applied view according to the preferred embodiment of the present invention, illustrating gas circulation.
Figure 4:
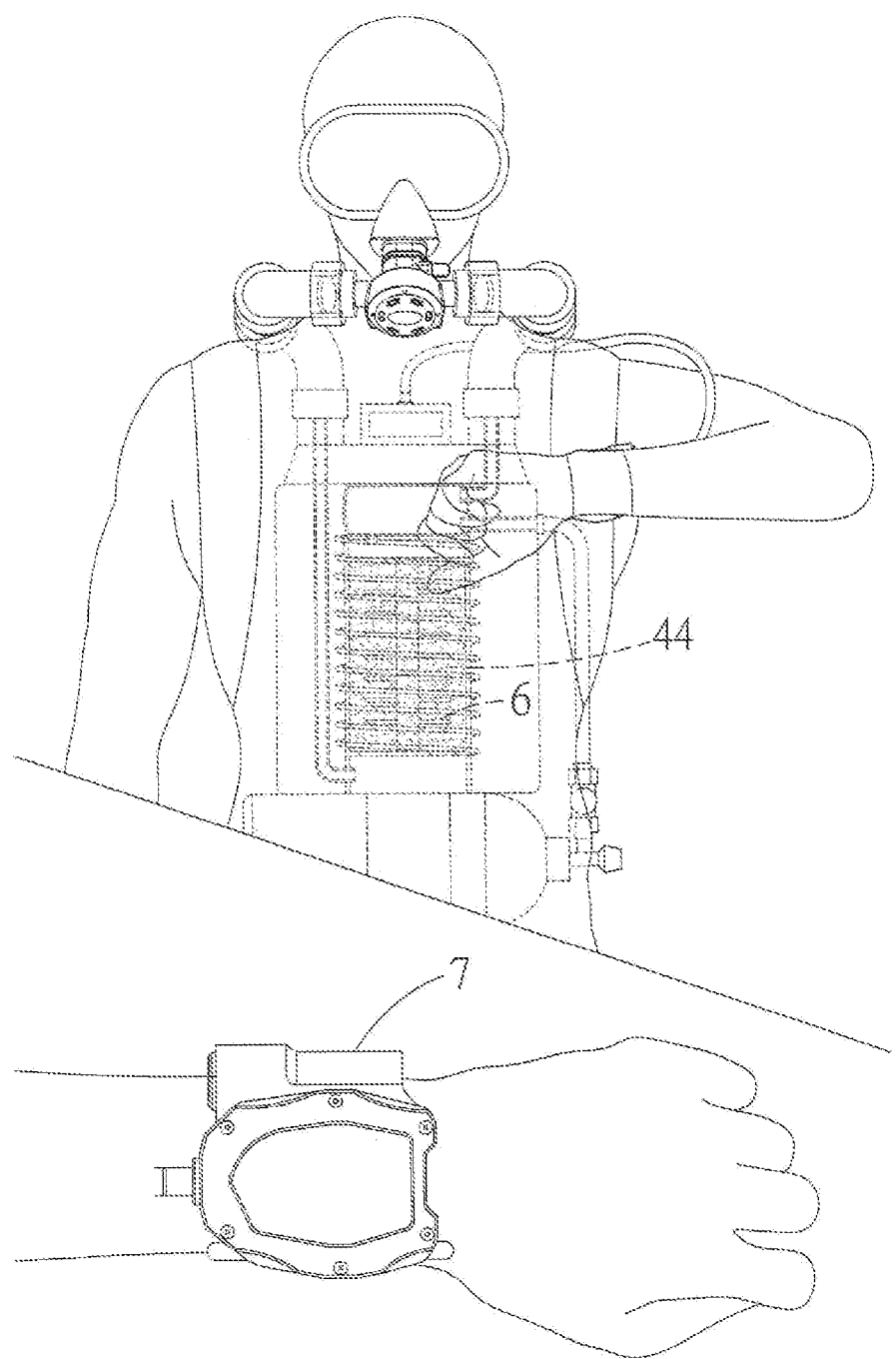
FIG. 4 is an applied view according to the preferred embodiment of the present invention, illustrating monitoring.

As shown in FIG. 1 and FIG. 2, which are a schematic drawing and a structural diagram of a rebreather 100 according to a preferred embodiment of the present invention, the rebreather 100 comprises:

an oxygen supplying element 1, in the present embodiment implemented as, for example, a high-pressure pure oxygen cylinder;

a gas mixing portion 2 deposited at one side of the oxygen supplying element 1 and connected to the oxygen supplying element 1;

a first controller 11 deposited on the oxygen supplying element 1, and in the present embodiment implemented as, for example, a solenoid valve;

a breath connecting element 3 deposited at one side of the gas mixing portion 2 and connected to the gas mixing portion 2, and in the present embodiment implemented as, for example, a mouthpiece;

a scrubber 4 deposited at one side of the breath connecting element 3 and connected to the breath connecting element 3, wherein the scrubber 4 has an outer barrel 41, a gas introducing portion 42 deposited at one end of the outer barrel 41, a gas exhausting portion 43 deposited on another end of the outer barrel 41 opposite to the end having the gas introducing portion 42, and a carbon-dioxide absorbent 44 deposited inside the outer barrel 41, in which the carbon-dioxide absorbent 44 may be for example a zeolite-based absorbent in the present embodiment, and in which the gas introducing portion 42 and the breath connecting element 3 are connected to each other, while the gas introducing portion 42 and the gas mixing portion 2 are connected to each other;

an absorbent heating element 5 deposited on the scrubber 4 and configured to heat the absorbent be means of electric power, infrared rays, chemical energy, hot water, or thermal exchange, wherein the means may be for example electric power implemented by heating wire wound around the outer barrel 41;

a first check valve 31 deposited between the gas mixing portion 2 and the breath connecting element 3, and configured to restrict gas to flow in the direction from the gas mixing portion 2 to the breath connecting element 3;

a second check valve 32 deposited between the breath connecting element 3 and the scrubber 4, and particularly located between the absorbent heating element 5 and the breath connecting element 3 in the present embodiment, so as to restrict gas to flow in the direction from the breath connecting element 3 to the scrubber 4;

a temperature detecting component 6 deposited inside the scrubber 4, and in the present embodiment implemented as plural thermometers arranged into a matrix in the outer barrel 41;

a state display 7 connected to the temperature detecting component 6, and in the present embodiment implemented as, for example, a screen that displays temperatures measured by the temperature detecting component 6; and a power supplying portion 8 electrically connected to the absorbent heating element 5 and the state display 7, and in the present embodiment implemented as, for example, a rechargeable battery deposited beside the scrubber 4, wherein the rechargeable battery may be charged through wire or wireless.

Moreover, in the present embodiment, between the oxygen supplying element 1 and the gas mixing portion 2, between the gas mixing portion 2 and the breath connecting element 3, between the breath connecting element 3 and the scrubber 4, and between the scrubber 4 and the gas mixing portion 2, there are pipes for connecting the components.

With the configuration described above, the rebreather 100 of the present invention advantageously has prolonged duration of use, and detailed explanation will be given below.

Referring to FIG. 1 through FIG. 4, as can be seen from these various drawings, in use of the foregoing embodiment of the present invention, a user equipped with the rebreather 100 may hold the breath connecting element 3 in his/her mouth to facilitate his/her breath during scuba diving. When the user exhales gas, the first check valve 31 and the second check valve 32 restrict the exhaled gas to flow toward the scrubber 4.

The exhaled gas then enters the outer barrel 41 through the gas introducing portion 42 to received treatment by which carbon dioxide contained therein are removed by the carbon-dioxide absorbent 44 through absorption. The treated, carbon-dioxide-free, exhaled gas is then guided by the gas exhausting portion 43 into the gas mixing portion 2. At this time, the first controller 11 controls the oxygen supplying element 1 to feed a proper amount of pure oxygen into the gas mixing portion 2, so that the pure oxygen and the treated, exhaled gas mix with each other to form supply gas that can be consumed by the user. The foregoing gas mixing may perform at a ratio that causes the resulting gas has an oxygen content equal to the oxygen content in the atmospheric air. For example, in the resulting gas, the oxygen content is 20%.

In addition, the adsorption efficiency of the carbon-dioxide absorbent 44 is in positive correlation with the temperature, which means the adsorption efficiency is better when the temperature is higher. Although the temperature of the exhaled gas upon exhalation is close to the user's body temperature, it can be cooled by seawater while traveling along the pipes and can eventually become as cool as seawater. At such a lower temperature, the efficiency for absorbing carbon dioxide can be degraded.

Thus, the carbon-dioxide absorbent 44 in the scrubber 4 of the present invention will be heated by the absorbent heating element 5, and therefore shows improved adsorption efficiency with respect to carbon dioxide as an outcome of its increased temperature. Additionally, as the adsorption efficiency gets improved, the duration of use of the oxygen supplying element 1 is prolonged, thereby enhancing the overall duration of use of the rebreather 100.

Based on the principle that the increased adsorption efficiency of the scrubber 4 indicates the raised temperature, the temperature detecting component 6 can learn how well adsorption performs by detecting the temperature in the scrubber 4. Moreover, since the temperature detecting component 6 is herein implemented as plural thermometers arranged into a matrix, the temperature state it detects and shows through the state display 7 is more accurate and complete. The displayed information may be, for example, "Current average temperature: 35° C." This enables the user to monitor the adsorption performance of the scrubber 4 and ensure underwater safety during diving. The state display 7 and the absorbent heating element 5 can both be powered by the power supplying portion 8 to operate.

Figure 5:
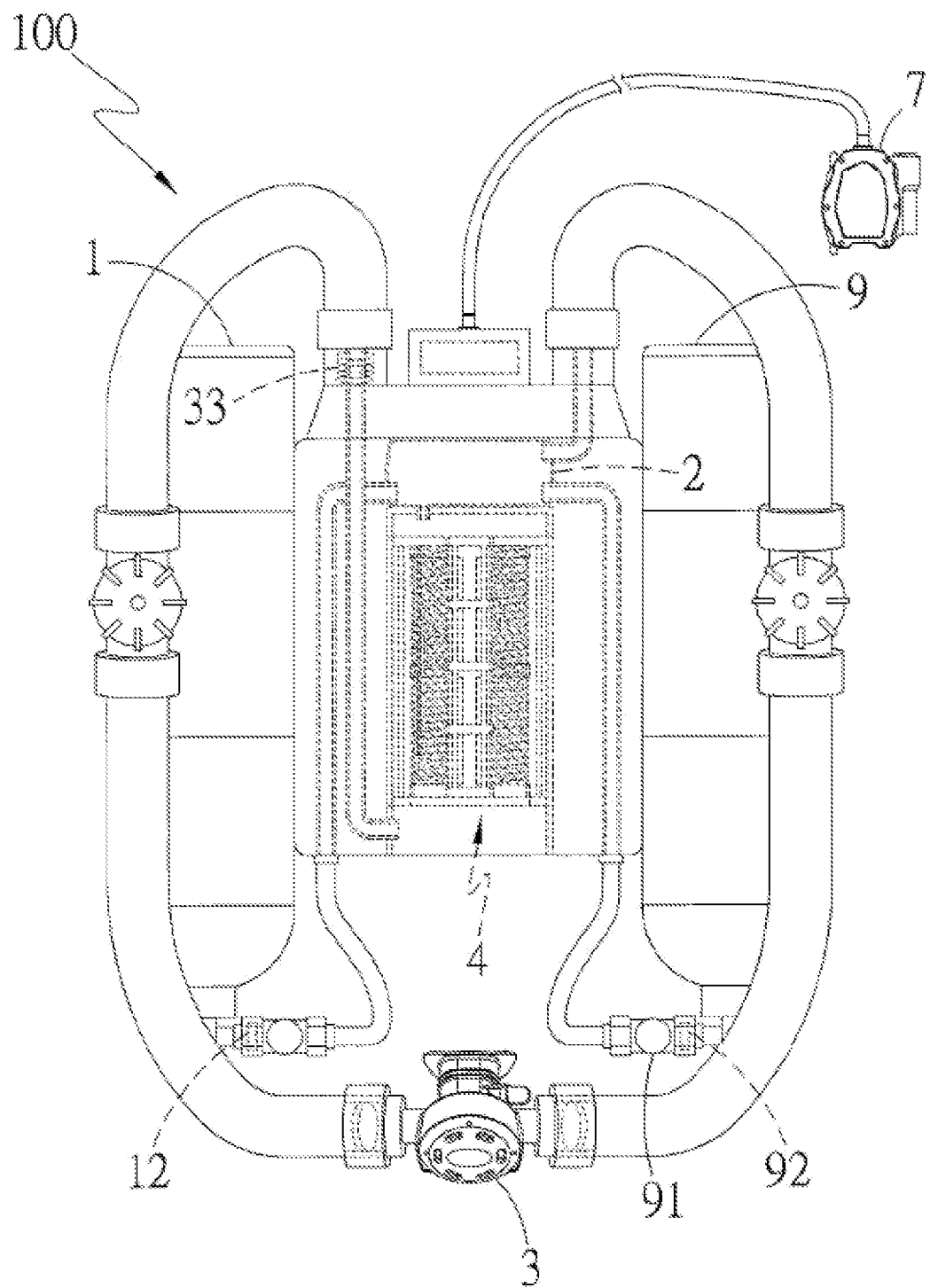
FIG. 5 is a schematic drawing of the apparatus according to an alternative preferred embodiment of the present invention.
Figure 6:
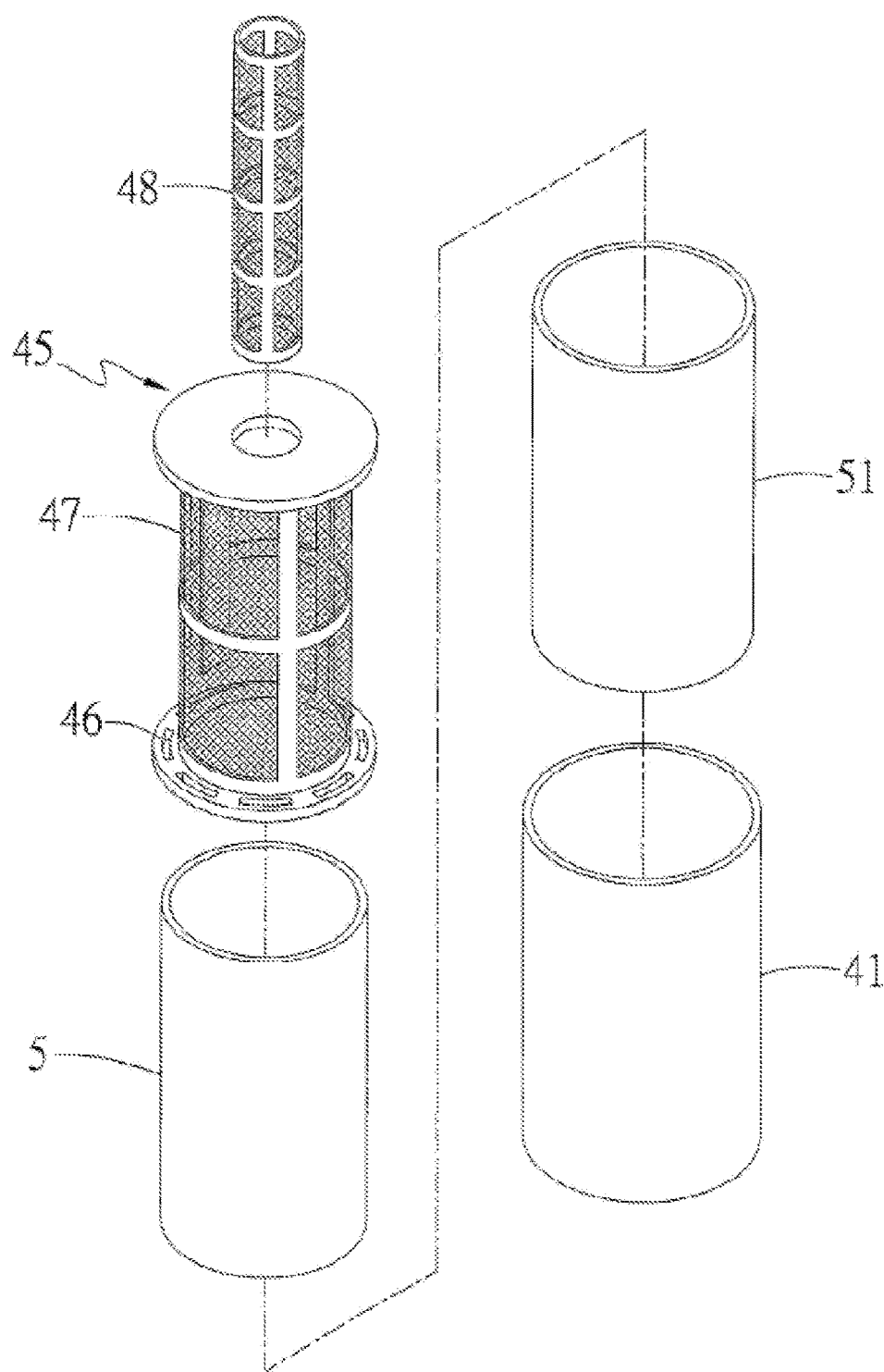
FIG. 6 is an exploded view of a part of the apparatus according to the second preferred embodiment of the present invention.
Figure 7:
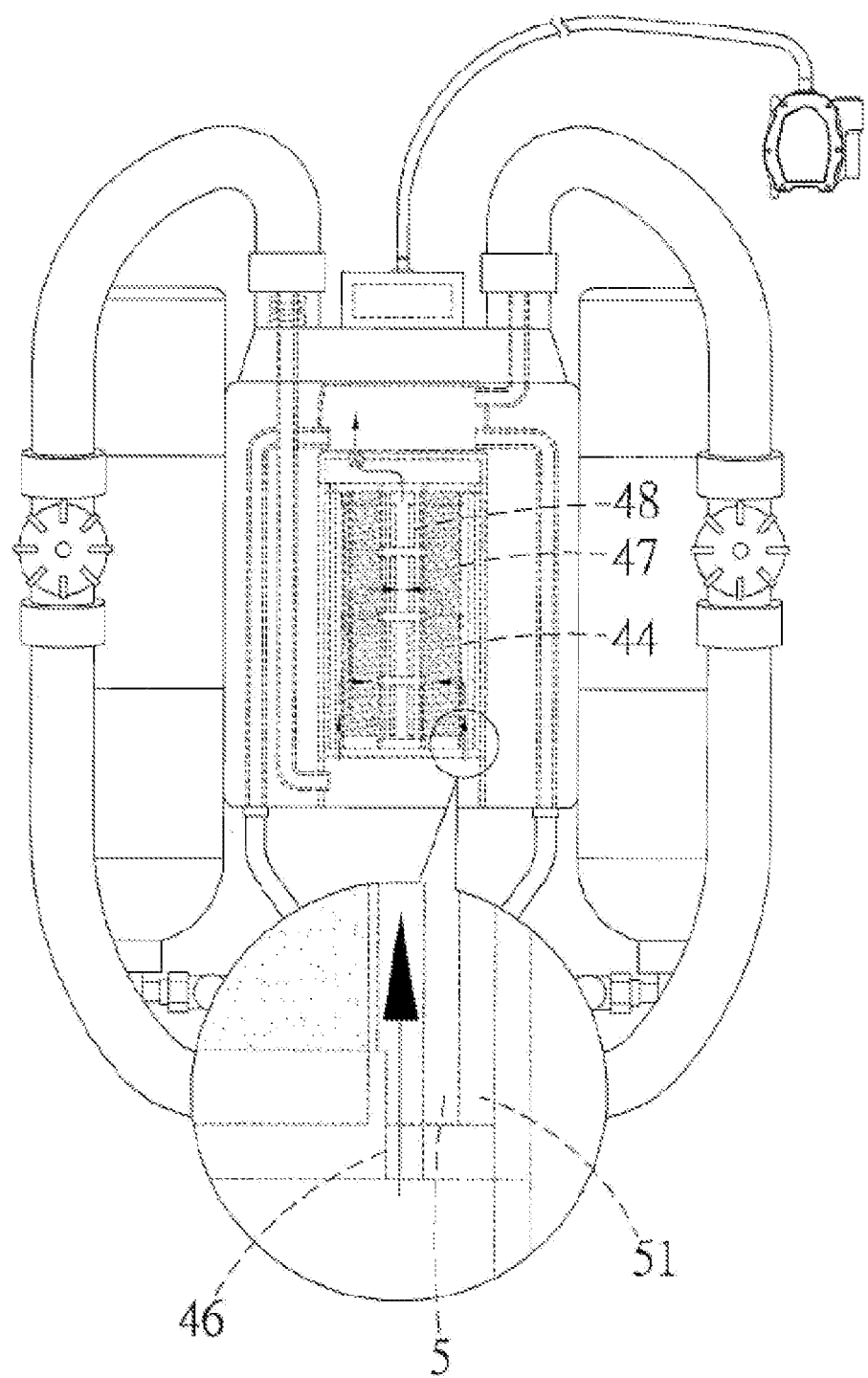
FIG. 7 is a schematic drawing of the apparatus according to the second preferred embodiment of the present invention, illustrating adsorption.

Further referring to FIG. 5 through FIG. 7, as can be seen from these various drawings, in use of a second embodiment of the present invention, the rebreather 100 is similar to its counterpart in the previous embodiment, except that the gas mixing portion 2 has an air supply element 9 connected thereto, and the air supply element 9 is controlled by a second controller 91. The air supply element 9 is configured to store a compressed version of the atmospheric air gas, which works with the pure oxygen supplied by the oxygen supplying element 1 to form supply gas that is more suitable for human breath. Furthermore, the oxygen supplying element 1 has an oxygen-level detecting element 12 connected thereto. The air supply element 9 is provided with an air-level detecting element 92 that is connected to the state display 7.

Additionally, in the present embodiment, a gas heating element 33 is deposited between the breath connecting element 3 and the scrubber 4. The scrubber 4 has an outer barrel 41, an inner barrel 45 deposited inside the outer barrel 41, a gas inlet portion 46 deposited between the outer barrel 41 and the inner barrel 45, a gas inlet plane 47 defined on the wall of the inner barrel 45, a gas exhausting pipe 48 deposited inside the inner barrel 45, and a carbon-dioxide absorbent 44 deposited between the inner barrel 45 and the gas exhausting pipe 48. The gas inlet portion 46 and the breath connecting element 3 are connected to each other, while the gas exhausting pipe 48 and the gas mixing portion 2 are connected to each other. The absorbent heating element 5 may be, for example, a heating plate installed on the outer side of the inner barrel 45. Meanwhile, an insulating element 51 is deposited between the absorbent heating element 5 and the outer barrel 41. While the above description has been made for explaining the present invention, it is to be noted that the form of the scrubber 4 is not limited thereto.

When the user exhales, the exhaled gas is first heated by the gas heating element 33 so that the temperature of the exhaled gas is raised, thereby further enhancing the adsorption efficiency of the carbon-dioxide absorbent 44. After entering the scrubber 4, the exhaled gas enters the outer barrel 41 through the gas inlet portion 46, and then passes through the gas inlet plane 47 in the outer barrel 41 to enter the inner barrel 45, where the carbon-dioxide absorbent 44 performs adsorption, after which the exhaled gas is eventually guided into the gas mixing portion 2 by the gas exhausting pipe 48. Since the surface area of the wall of the inner barrel 45 is much larger than the surface area of the end of the outer barrel 41, the contact area between the exhaled gas and the carbon-dioxide absorbent 44 can be significantly increased, so as to even further enhance the adsorption efficiency of the carbon dioxide and in turn prolong the duration of use of the rebreather 100. Besides, with the insulating element 51, the heat provided by the absorbent heating element 5 can be better built up within the scrubber 4.

In addition to the temperature in the scrubber 4, the remaining oxygen level and the remaining air level as detected by the oxygen-level detecting element 12 and the air-level detecting element 92, respectively, can be shown to the user in a real-time manner through the state display 7. In the present embodiment, the oxygen-level detecting element 12 and the air-level detecting element 92 may each be, for example, a pressure detector capable of measuring the pressure in the high-pressure gas cylinder. This even improves the visibility of the operation of the rebreather 100, making its use more convenient and safer.

What is claimed is:

1. A diving rebreather apparatus, comprising:
   an oxygen supplying element;
   a gas mixing portion, deposited at one side of the oxygen supplying element, connected to the oxygen supplying element, and configured to receive oxygen from the oxygen supplying element;
   a breath connecting element, deposited at one side of the gas mixing portion, connected to the gas mixing portion, and configured to receive supply gas from the gas mixing portion for a using the diving rebreather apparatus to inhale;
   a scrubber, deposited at one side of the breath connecting element, connected to the breath connecting element and the gas mixing portion, and configured to receive exhaled gas exhaled by the user from the breath connecting element, to treat the exhaled gas by removing carbon dioxide from the exhaled gas through adsorption, and to guide the treated exhaled gas into the gas mixing portion;
   an absorbent heating element, deposited on the scrubber and configured to heat the scrubber;
   a temperature detecting component, deposited inside the scrubber;
   a state display, connected to the temperature detecting component and configured to receive a temperature state measured by the temperature detecting component; and
   a power supplying portion, electrically connected to the absorbent heating element and the state display;
   wherein the scrubber has an outer barrel, an inner barrel deposited within the outer barrel, a gas inlet portion deposited between the outer barrel and the inner barrel, a gas inlet plane defined on a wall of the inner barrel, a gas exhausting pipe deposited in the inner barrel, and a carbon-dioxide absorbent deposited between the inner barrel and the gas exhausting pipe, in which the gas inlet portion and the breath connecting element are connected to each other, while the gas exhausting pipe and the gas mixing portion are connected to each other.

2. The diving rebreather apparatus of claim 1, wherein the absorbent heating element is provided with an insulating element.

3. The diving rebreather apparatus of claim 1, further comprising a gas heating element deposited between the breath connecting element and the scrubber and configured to heat the exhaled gas before the exhaled gas enters the scrubber.

4. The diving rebreather apparatus of claim 1, wherein the oxygen supplying element is provided with a first controller, which is configured to control an amount of oxygen supplied by the oxygen supplying element.

5. The diving rebreather apparatus of claim 1, wherein the oxygen supplying element is provided with an oxygen-level detecting element that is connected to the state display.

6. The diving rebreather apparatus of claim 1, wherein the gas mixing portion is configured to be connected to an air supply element.

7. The diving rebreather apparatus of claim 6, wherein the air supply element is provided with a second controller.

8. The diving rebreather apparatus of claim 6, wherein the air supply element is provided with an air-level detecting element that is connected to the state display.

\* \* \* \* \*